United States Patent [19]
Cai et al.

[11] Patent Number: 6,114,165
[45] Date of Patent: Sep. 5, 2000

[54] UNIVERSAL TISSUE CULTURE FLASK

[76] Inventors: Xuejun Cai; Yalin Lin, both of 18249 73rd Ave NE. B-101, Kenmore, Wash. 98028; Guohe Lin, Xianmei, Leigo, Leizhou, China, 524241

[21] Appl. No.: 09/121,023

[22] Filed: Jul. 23, 1998

Related U.S. Application Data

[60] Provisional application No. 60/053,513, Jul. 23, 1997.

[51] Int. Cl.[7] .................................................. C12M 1/24
[52] U.S. Cl. ......................... 435/304.3; 215/40; 215/306
[58] Field of Search ............................. 435/288.1, 304.1, 435/304.3; 422/102; 215/40, 306, 315

[56] References Cited

U.S. PATENT DOCUMENTS

| | | | |
|---|---|---|---|
| 4,334,028 | 6/1982 | Carver . | |
| 4,534,483 | 8/1985 | Kassis et al. | 435/304.3 |
| 4,851,351 | 7/1989 | Akamine . | |
| 4,967,921 | 11/1990 | Pre et al. | 215/295 |
| 5,262,326 | 11/1993 | Jaeger et al. | 435/304.3 |
| 5,398,837 | 3/1995 | Degrassi . | |

FOREIGN PATENT DOCUMENTS

| | | | |
|---|---|---|---|
| 0 141 104 | 5/1985 | European Pat. Off. | 435/304.3 |
| 2 342 910 | 11/1977 | France . | |
| 24 53 858 | 5/1975 | Germany | 435/288.1 |
| 2 185 997 | 8/1987 | United Kingdom | 435/304.3 |

*Primary Examiner*—William H. Beisner

[57] ABSTRACT

The present invention improves performance of a flask used for microorganism, cell and tissue culture. The flask is composed of culture chamber, a wide oblong opening and a closure unit. The wide oblong opening eliminates the bottle neck restriction of conventional flasks and gives easy access to the culture chamber. The closure unit is constructed with a snap-on closure, a base and springs, which interconnect the closure and the main body of flask through the base. The springs function to maintain the closure at the opening position to facilitate culture operation. The problem of the screw-on closure that requires to be hold in a operator's hand is solved.

11 Claims, 3 Drawing Sheets

UNIVERSAL TISSUE CULTURE FLASK

This application claims the priority benefit of provisional application No. 60/053,513, filed on Jul. 23, 1997.

BACKGROUND OF THE INVENTION

For a long time, culture dishes and flasks have been used for microorganism, cell and tissue culture. Culture dishes consist of a bottom dish to contain medium for cell growth and a removable cover. Although the removable cover provide a convenient access, cells are often contaminated by other microorganisms while the cover is removed during culture operation. To solve this problem, culture flasks were developed. The culture flasks typically have a culture chamber, a small tubular opening located on one side of the flask and a corresponding screw-on closure. This design prevents direct exposure of cells to dust, bacteria and yeast. Cell contamination is largely reduced. The screw-on closure and tubular opening are widely used in all flasks including prior arts (U.S. Pat. Nos. 4,334,028; 4,851,351 and 5,398,837).

Although application of the small tubular opening resolves the problem of contamination, a complication of the small opening causes a major difficulty for culture operations, such as insertion of a pipette through the opening for applying culture media. An inaccessible area is created in the culture chamber, particularly on the area adjacent to the opening. The problem becomes more severe during operations such as scraping cells off the flask, picking up colonies where they develop during culture process. Carver (U.S. Pat. No. 4,334,028) attempted to solve this problem by introducing a frangible zone on top of the flask. Culture procedures are accomplished through the opening on top of the flask created by cutting or breaking the frangible zone. When these flasks are used, cells are potentially contaminated through the broken wall. In addition, extra equipment and effort are also required to create the opening.

Cell culture procedure is a time-consuming manual operation. Generally it takes much longer time to accomplish when flasks are used for these problems related to the small tubular opening and closure. First, it consumes a longer time to perform all culture procedures through the small tubular opening. Second, the screw-on closure is usually required to be hold in a hand in order to avoid the closure being contacted with other objects and contaminated. A user has to perform culture procedures with a single hand. Consequently, these factors greatly reduce culture operation efficiency.

SUMMARY OF THE INVENTION

The objects of this invention is to provide a flask having both advantages of culture dish and flask. Specifically, this flask is designed to have features of easy access for culture operation and contamination proof. In this invention, these objects are accomplished by using a wide oblong opening located on one side of the flask, a corresponding shape of closure unit consisting of the closure, the springs and the base. The oblong opening is an extrusion from main body of the flask. The opening width is capable of extending up to 100% of that of the chamber width, which essentially eliminates the restriction of the opening that all other flasks inherit. The culture chamber of this invention can be readily accessed for varieties of culture operation. Because the opening is located on the side, the design avoids direct exposure of cells to offenders in air and subsequently minimize the possibility of contamination during culture operation.

The closure, springs and base assemble a functional closure unit for this flask. The closure is a snap-on, oblong cap. The springs consists of several plastic folds. The springs join the closure to the base which is then forced to clamp on the lower portion the opening. A functional closure unit is formed. The springs are compressed or extended to assist maneuvers of the closure. The closure is maintained to be in open position by bending it backward with a support of the springs. Thus, a user does not require to hold the closure within a hand during entire operation. Both hands are available to coordinate culture procedures.

A locking mechanism is also provided to secure the closure and maintain sterile environment of the culture chamber.

DETAILED DESCRIPTION

Figure 1:
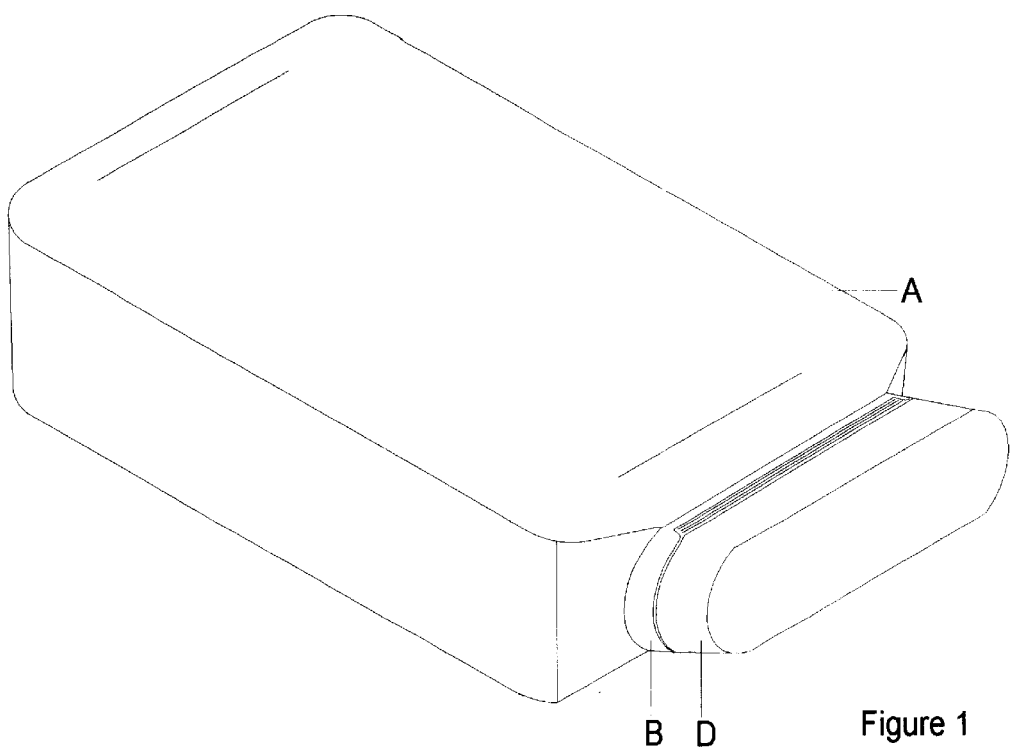
FIG. 1 is a perspective view of the top of the culture flask according to the current invention.
Figure 2:
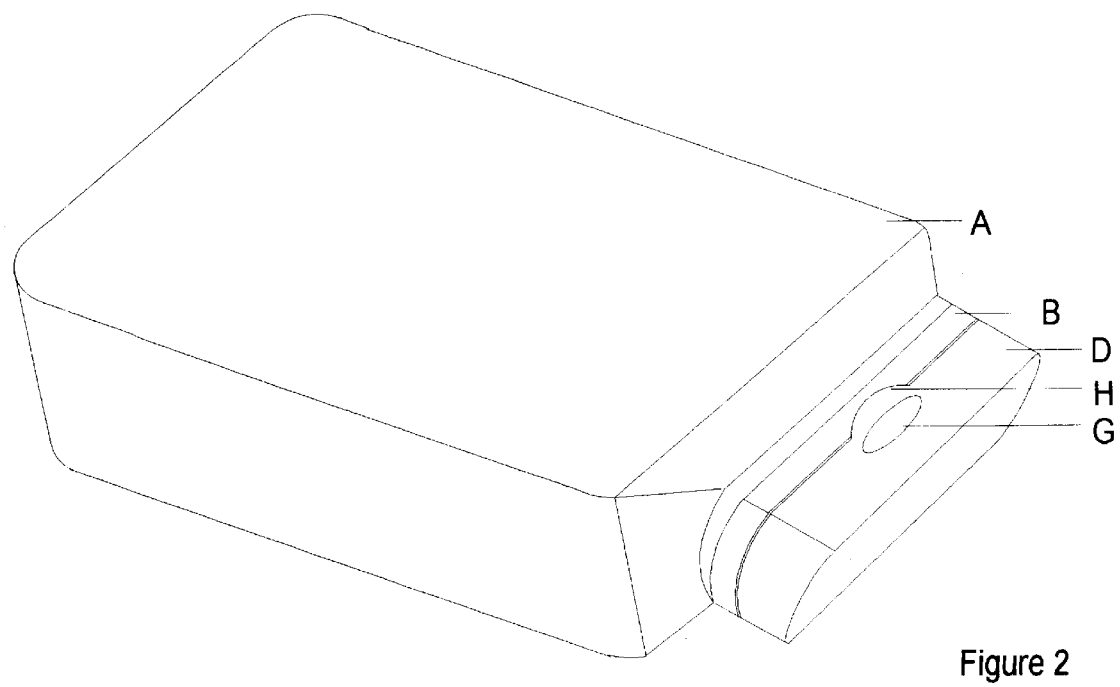
FIG. 2 is a perspective view of the bottom of the culture flask shown in the FIG. 1.
Figure 3:
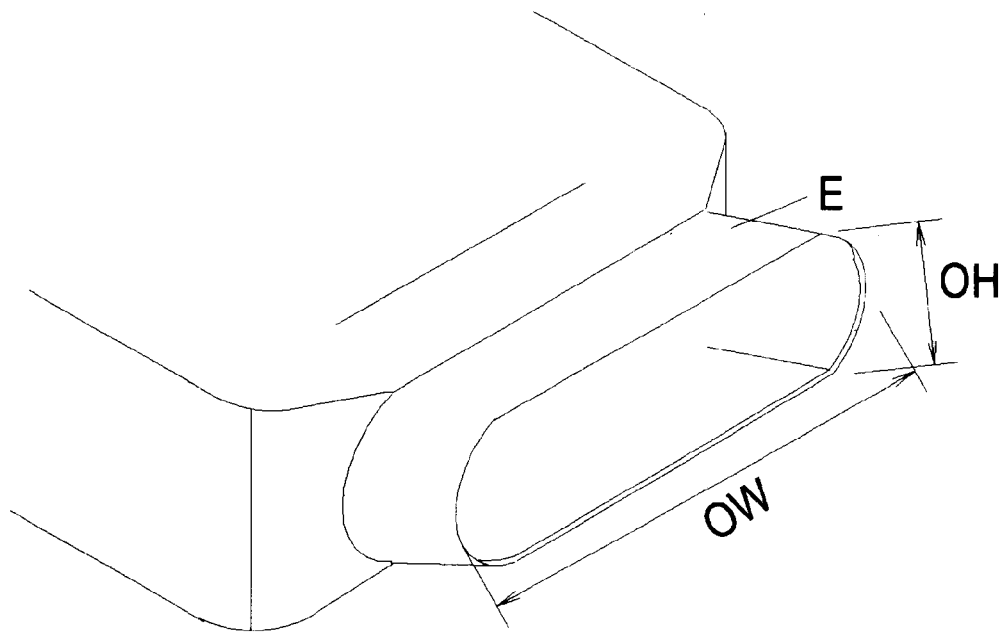
FIG. 3 and FIG. 4 show the opening from the top and bottom respectively. The complete closure unit has been removed from the opening.
Figure 4:
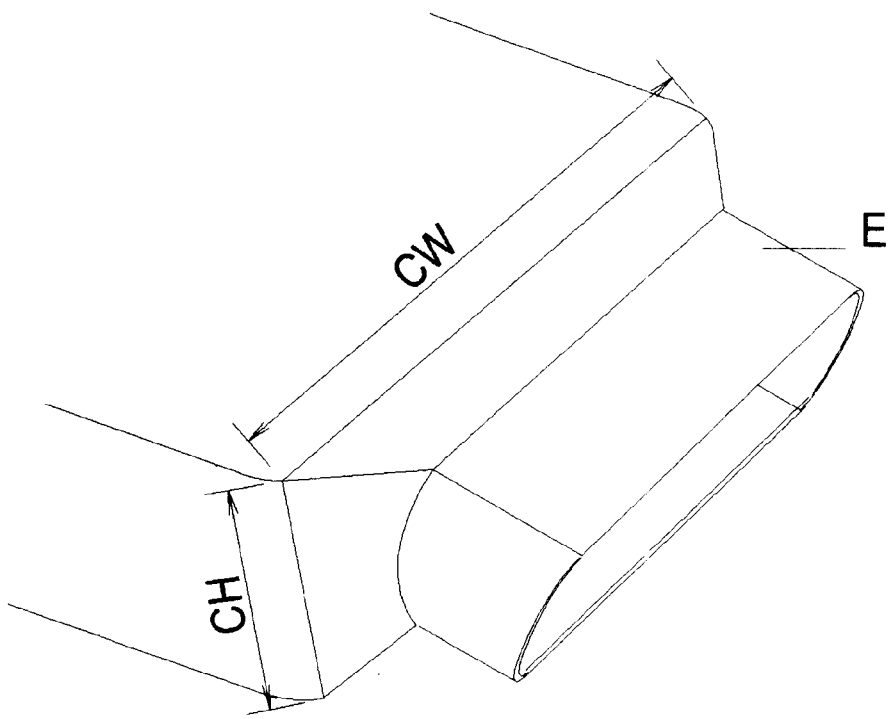
Figure 5:
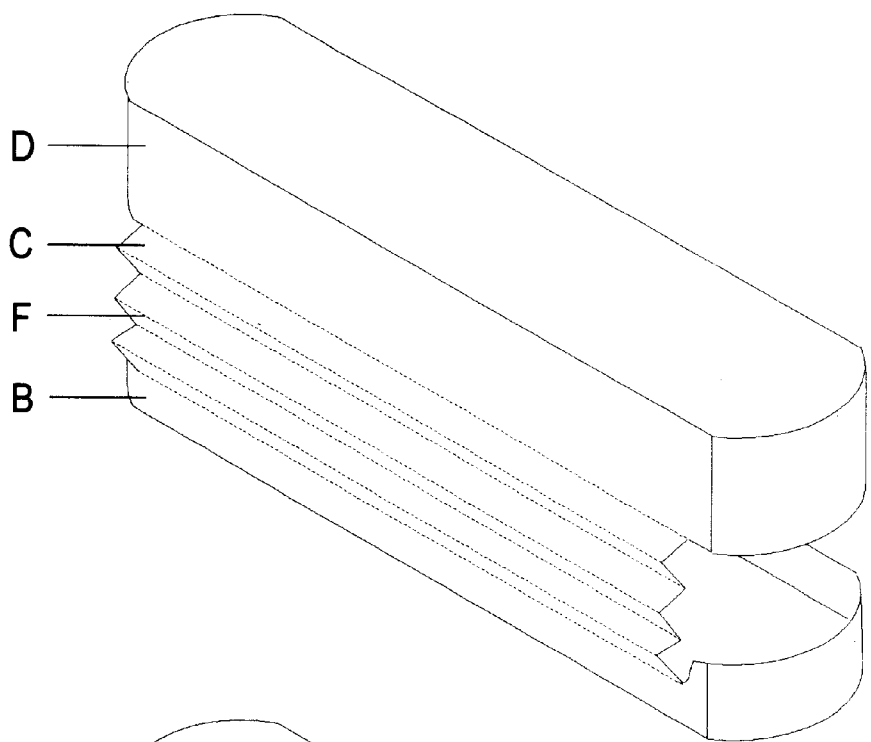
FIG. 5 is a perspective view of the closure unit. The springs are in a partially extensive position.
Figure 6:
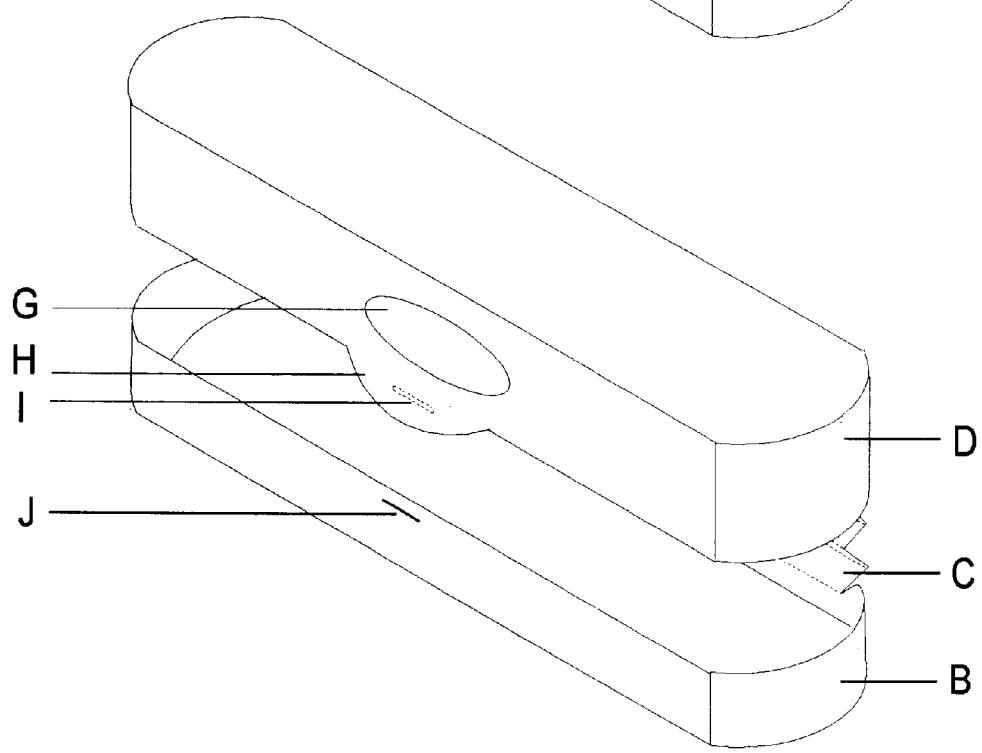
FIG. 6 illustrates the locking mechanism of the closure.

A culture flask of the current invention will be described thereunder with reference letters to the drawings. The culture chamber(A) and opening (E) are made from transparent plastic such as polystyrene or polymethylmethacryate. Although the opening may he constructed in oblong or rectangle shape, the oblong shape is preferred for its pleasure appearance. The opening(E) is extruded from the culture chamber(A) and has angle upward 20 to 30 degrees. As shown in the FIG. 3 and FIG. 4, the opening width (OW) may extend to 100 percent of the chamber width(CW), with preference of 40% to 80% of the chamber width. The opening height (OH) ranges from 70% to 100% of the chamber height(CH).

As shown in the FIGS. 1, 2, 5 and 6, the closure(D) is connected to the base(B) through the springs (C). Flexible plastic such as polypropylene or polyallomer is a suitable material for the closure unit. The top interior dimension of the base(B) is 0.1 to 0.2 mm less than outer dimension of the opening(E). The lower interior dimension of the base(B) is 0.25 to 1 mm larger than outer dimension of the opening (E). The inclination is formed in the interior wall of the base. Therefore, the base (B) can be pushed down to the bottom of the opening(E) until it is clamped to a fixative position. The inner dimension of the closure (D) is approximately 0.5 to 1 mm larger than that of the outer dimension of the opening(E) to create a space for gas exchange between the culture chamber of the flask and an incubator. In addition, this closure may be also a vent-type cap.

Typically, the springs (C) is composed of 4 to 8 plastic folders. Each fold has the thickness ranging from 0.2 mm to 0.5 mm and the width ranging from 3 to 5 mm. The number and size of the folds depend on size of the flasks. The springs is extended upward 12 to 30 mm to aid opening the closure. The folding line (F) is considerably thinner than the fold so that the springs could be well compressed when the closure seals the opening.

A locking mechanism is provided to secure the closure. As shown in the FIG. 6, the outer edge of the closure is extended to form a flap(H). The locking mechanism is formed from a indention(I) locating interior surface of the flap and a corresponding latch(J) projecting from the base(B). When the closure is pushed down to seal the opening, the latch snaps the indention beneath the flap and locks the closure. The closure can be easily unlocked by lifting the flap with fingers. An oval concavity(G) guides a finger to grasp the closure.

What is claimed is:

1. A culture flask comprising:
    a bottom wall, a top wall and sidewall connecting the bottom wall and top wall to define a culture chamber;
    an elongated extrusion extending from the sidewall defining an oblong opening in communication with the culture chamber, the extrusion extending at an upward angle relative to the bottom wall; and
    a closure corresponding to the oblong opening of the extrusion so as to seal the culture chamber.

2. A flask as defined in claim 1, wherein the width of the oblong opening extends to 100% of the width of the culture chamber.

3. A flask as defined in claim 1, wherein the width of the oblong opening extends to 40% to 80% of the width of the culture chamber.

4. A flask as defined claim 1, wherein the height of said oblong opening ranges from 70% to 100% of the height of the culture chamber.

5. A flask as defined in any one of the proceeding claims wherein the flask is made of transparent plastic.

6. A flask as defined in claim 1, wherein the closure snaps on to the opening.

7. A flask as defined in claim 1, wherein the closure includes a means to retain the closure to the flask.

8. A flask as defined in claim 7, wherein said retaining means includes plastic springs and a base.

9. A flask as defined in claim 8, wherein said plastic springs consist of multiple plastic folds whereby said plastic springs can be compressed or extended to assist maneuvering of the closure.

10. A flask as defined in claim 8, wherein said base is securely fastened to the extrusion at a portion which connects with the culture chamber.

11. A flask as defined in any one of claims 6 to 10, wherein said closure is made of flexible plastic.

* * * * *